United States Patent
Sawaki et al.

(10) Patent No.: US 11,484,313 B2
(45) Date of Patent: Nov. 1, 2022

(54) STAPLE REINFORCEMENT FOR SURGICAL STAPLER

(71) Applicant: GUNZE LIMITED, Ayabe (JP)

(72) Inventors: Takashi Sawaki, Kyoto (JP); Yasuhiro Ueno, Kyoto (JP); Junki Ikeda, Kyoto (JP)

(73) Assignee: GUNZE LIMITED, Kyoto (JP)

( * ) Notice: Subject to any disclaimer, the term of this patent is extended or adjusted under 35 U.S.C. 154(b) by 0 days.

(21) Appl. No.: 17/099,317

(22) Filed: Nov. 16, 2020

(65) Prior Publication Data

US 2021/0177416 A1     Jun. 17, 2021

(30) Foreign Application Priority Data

Dec. 12, 2019    (JP) .............................. JP2019-224762

(51) Int. Cl.
| | |
|---|---|
| A61B 17/072 | (2006.01) |
| A61B 17/068 | (2006.01) |
| B32B 5/24 | (2006.01) |
| B32B 27/36 | (2006.01) |

(Continued)

(52) U.S. Cl.
CPC .... *A61B 17/07292* (2013.01); *A61B 17/0686* (2013.01); *B32B 5/20* (2013.01); *B32B 5/245* (2013.01); *B32B 23/10* (2013.01); *B32B 27/36* (2013.01); *A61B 2017/07257* (2013.01);

(Continued)

(58) Field of Classification Search
CPC ........ A61B 17/07292; A61B 17/06166; A61B 17/0686; A61B 2017/07257; A61B 2017/00004; A61B 2017/00526; A61B 2017/00951; A61L 17/12; A61L 17/145; A61L 2400/14; B32B 5/20; B32B 5/245;

(Continued)

(56) References Cited

U.S. PATENT DOCUMENTS

| | | | | |
|---|---|---|---|---|
| 5,542,594 | A | * | 8/1996 | McKean .......... A61B 17/07207 227/19 |
| 6,260,699 | B1 | * | 7/2001 | Kaplan .................. A61L 27/34 206/339 |

(Continued)

FOREIGN PATENT DOCUMENTS

| | | |
|---|---|---|
| JP | 08-047526 | 2/1996 |
| JP | 4675237 B | 4/2011 |
| JP | 02012065699 A * | 4/2012 ........... A61L 31/146 |

OTHER PUBLICATIONS

Hashimoto Ayumi, Reduction of air leaks in a canine model of pulmonary resection with a new staple-line buttress, published on The Journal of Cardiovascular Surgery, vol. 142, Issue 2, Aug. 2011, pp. 366-371 (Year: 2011).*

*Primary Examiner* — Robert F Long
*Assistant Examiner* — Eduardo R Ferrero
(74) *Attorney, Agent, or Firm* — Hamre, Schuamnn, Mueller & Larson, P.C.

(57) ABSTRACT

The present invention aims to provide a staple reinforcement for a surgical stapler that can be used in surgical staplers of various sizes, is easily passed through ports, and is less likely to shift during operation of the surgical stapler. Provided is a staple reinforcement for a surgical stapler, including a fabric layer containing a bioabsorbable material and a sponge layer containing a water-soluble polymer, the fabric layer and the sponge layer being integrally laminated.

6 Claims, 1 Drawing Sheet

(51) Int. Cl.
*B32B 23/10* (2006.01)
*B32B 5/20* (2006.01)
(52) U.S. Cl.
CPC ............... *B32B 2307/7163* (2013.01); *B32B 2307/7166* (2013.01)
(58) Field of Classification Search
CPC . B32B 23/10; B32B 27/36; B32B 2307/7163; B32B 2307/7166
See application file for complete search history.

(56) References Cited

U.S. PATENT DOCUMENTS

| | | | | |
|---|---|---|---|---|
| 6,330,965 | B1* | 12/2001 | Milliman | A61B 17/105 227/176.1 |
| 6,962,594 | B1* | 11/2005 | Thevenet | A61L 31/148 606/151 |
| 8,372,433 | B2* | 2/2013 | Shinoka | A61L 27/56 424/484 |
| 9,272,406 | B2* | 3/2016 | Aronhalt | A61B 17/0682 |
| 10,463,469 | B2* | 11/2019 | Nakayama | A61L 27/58 |
| 2004/0254272 | A1* | 12/2004 | Ando | C08F 2/00 524/107 |
| 2006/0088589 | A1* | 4/2006 | Gorman | B32B 5/026 424/455 |
| 2007/0049953 | A2* | 3/2007 | Shimoji | A61B 17/07207 606/151 |
| 2009/0001122 | A1* | 1/2009 | Prommersberger | B29C 39/22 227/176.1 |
| 2009/0246238 | A1* | 10/2009 | Gorman | A61L 15/64 424/94.64 |
| 2012/0080498 | A1* | 4/2012 | Shelton, IV | A61B 17/07207 227/180.1 |
| 2012/0083836 | A1* | 4/2012 | Shelton, IV | A61B 17/07207 206/339 |
| 2012/0187179 | A1* | 7/2012 | Gleiman | A61B 17/072 227/176.1 |
| 2012/0241491 | A1* | 9/2012 | Aldridge | A61B 17/105 227/175.1 |
| 2012/0241492 | A1* | 9/2012 | Shelton, IV | A61B 17/00491 227/175.1 |
| 2012/0241497 | A1* | 9/2012 | Mandakolathur Vasudevan | A61B 17/07292 227/176.1 |
| 2012/0241499 | A1* | 9/2012 | Baxter, III | A61B 17/105 227/176.1 |
| 2012/0241502 | A1* | 9/2012 | Aldridge | A61B 17/00491 227/176.1 |
| 2012/0241505 | A1* | 9/2012 | Alexander, III | A61B 17/072 227/179.1 |
| 2012/0253298 | A1* | 10/2012 | Henderson | A61B 17/1155 604/93.01 |
| 2012/0273547 | A1* | 11/2012 | Hodgkinson | A61B 17/07292 227/176.1 |
| 2012/0318844 | A1* | 12/2012 | Shelton, IV | A61B 17/00234 227/176.1 |
| 2013/0105548 | A1* | 5/2013 | Hodgkinson | A61B 17/07292 227/176.1 |
| 2013/0112731 | A1* | 5/2013 | Hodgkinson | A61B 17/105 227/176.1 |
| 2013/0149343 | A1* | 6/2013 | Pesnell | A61L 15/42 424/94.64 |
| 2013/0153633 | A1* | 6/2013 | Casasanta, Jr. | A61B 17/1155 227/176.1 |
| 2013/0153638 | A1* | 6/2013 | Carter | A61B 17/1155 227/179.1 |
| 2013/0221065 | A1* | 8/2013 | Aronhalt | A61B 17/07292 227/176.1 |
| 2013/0256376 | A1* | 10/2013 | Barton | A61B 17/1155 227/176.1 |
| 2014/0128669 | A1* | 5/2014 | Kobayashi | A61B 1/0011 600/101 |
| 2014/0205637 | A1* | 7/2014 | Widenhouse | A61K 9/70 424/400 |
| 2014/0209658 | A1* | 7/2014 | Skalla | A61B 17/072 227/175.1 |
| 2014/0224857 | A1* | 8/2014 | Schmid | A61B 17/07292 227/176.1 |
| 2014/0291379 | A1* | 10/2014 | Schellin | A61B 17/068 227/176.1 |
| 2014/0291382 | A1* | 10/2014 | Lloyd | A61B 17/07207 227/176.1 |
| 2014/0367447 | A1* | 12/2014 | Woodard, Jr | A61B 17/00234 227/176.1 |
| 2015/0282810 | A1* | 10/2015 | Shelton, IV | A61B 17/0644 227/180.1 |
| 2015/0297218 | A1* | 10/2015 | Shelton, IV | A61B 17/0644 227/176.1 |
| 2015/0297225 | A1* | 10/2015 | Huitema | A61B 17/068 227/176.1 |
| 2016/0106427 | A1* | 4/2016 | Shelton, IV | A61B 17/0684 227/176.1 |
| 2016/0128694 | A1* | 5/2016 | Baxter, III | A61B 17/068 227/176.1 |
| 2016/0278774 | A1* | 9/2016 | Shelton, IV | A61B 17/068 |
| 2016/0278775 | A1* | 9/2016 | Shelton, IV | A61B 17/07207 |
| 2016/0278776 | A1* | 9/2016 | Shelton, IV | A61B 17/068 |
| 2016/0345976 | A1* | 12/2016 | González | A61B 17/07207 |
| 2017/0055986 | A1* | 3/2017 | Harris | A61B 17/07292 |
| 2017/0056567 | A1* | 3/2017 | Harris | A61B 17/064 |
| 2017/0086838 | A1* | 3/2017 | Harris | A61B 17/068 |
| 2018/0235626 | A1* | 8/2018 | Shelton, IV | A61B 17/07292 |
| 2018/0353659 | A1* | 12/2018 | Widenhouse | A61B 17/07292 |

* cited by examiner

STAPLE REINFORCEMENT FOR SURGICAL STAPLER

TECHNICAL FIELD

The present invention relates to a staple reinforcement for a surgical stapler that can be used in surgical staplers of various sizes, is easily passed through ports, and is less likely to shift during operation of the surgical stapler.

BACKGROUND ART

Surgical staplers containing many staples have been used in stapling of tissue. However, use of such devices in a tissue such as the lung may cause an air leak from the stapled portion, and use of them in a fragile tissue may cause damage, rupture, or the like of the tissue.

In order to prevent an air leak, a bodily fluid leak, and tissue damage, bioabsorbable reinforcement materials have been used together with surgical staplers (for example, Patent Literatures 1 and 2). The reinforcement materials of Patent Literatures 1 and 2 have a tubular structure formed by sewing two opposite sides of one bioabsorbable nonwoven fabric sheet together, or by stacking two bioabsorbable nonwoven fabric sheets or one bioabsorbable nonwoven fabric sheet and one stretchable knitted fabric sheet and sewing two opposite sides together. The reinforcement materials are mounted on a surgical stapler by inserting the end of the cartridge of the surgical stapler into the tube, and stapled together with tissue for tissue reinforcement. The reinforcement materials have high workability because unnecessary parts can be removed after reinforcement by pulling threads extending from the reinforcement materials. Moreover, the reinforcement materials, which are made of bioabsorbable nonwoven fabric, are ultimately absorbed in the living body after reinforcement is no longer needed.

CITATION LIST

Patent Literature

Patent Literature 1: JP H08-047526 A
Patent Literature 2: JP 4675237 B

SUMMARY OF INVENTION

Technical Problem

Conventional reinforcement materials used in surgical staplers have a tubular shape formed by combining a fabric for reinforcing tissue and a fabric having stretchability, and thus can make intimate contact with surgical staplers so as to avoid shifting during operation of the surgical staplers. However, since the cartridges of surgical staplers have various sizes, the reinforcement materials may fail to make intimate contact with a surgical stapler and shift depending on the size of the cartridge. Even a reinforcement material fit to the size of the cartridge can shift because of gaps near the seams of the fabrics.

In endoscopic surgery using a surgical stapler, multiple tubular ports are placed in the patient's body, through which tools such as an endoscope or a surgical stapler are inserted. When a surgical stapler is inserted into a port, a conventional reinforcement material, which is mounted to surround the cartridge of the surgical stapler, may get caught on the port. In addition, the surgical stapler mounted with the reinforcement material has a larger size due to the reinforcement material surrounding the cartridge. Such a surgical stapler cannot be passed through a port unless the port has a diameter larger than the size of the surgical stapler itself. To reduce patients' burden, there is a demand for a reinforcement material that can be passed through ports of smaller diameters.

In view of the above situation, the present invention aims to provide a staple reinforcement for a surgical stapler that can be used in surgical staplers of various sizes, is easily passed through ports, and is less likely to shift during operation of the surgical stapler.

Solution to Problem

The present invention relates to a staple reinforcement for a surgical stapler including a fabric layer containing a bioabsorbable material and a sponge layer containing a water-soluble polymer, the fabric layer and the sponge layer being integrally laminated.

The present invention is described in detail below.

As a result of intensive studies, the present inventors arrived at a reinforcement in which a sponge layer that exhibits adhesion when containing moisture is integrally laminated on a fabric containing a bioabsorbable material. The inventors found out that such a reinforcement can be attached to a working surface of a surgical stapler and is less likely to shift during operation of the surgical stapler. The inventors thus completed the present invention.

The staple reinforcement for a surgical stapler (hereinafter also referred to simply as the "reinforcement") of the present invention includes a fabric layer containing a bioabsorbable material.

A reinforcement containing a bioabsorbable material is highly safe because the reinforcement is ultimately absorbed in the living body after reinforcement is no longer needed, preventing foreign matter from remaining in the body for a long time. The "surgical stapler" herein includes not only linear surgical staplers but also circular surgical staplers.

Examples of the bioabsorbable material include synthetic absorbable polymers, for example, α-hydroxy acid polymers such as polyglycolide, polylactide (D, L, or DL), glycolide-lactide (D, L, or DL) copolymers, glycolide-ε-caprolactone copolymers, lactide (D, L, or DL)-ε-caprolactone copolymers, poly(p-dioxanone), and glycolide-lactide (D, L, or DL)-ε-caprolactone copolymers, and natural absorbable polymers such as collagen, gelatin, chitosan, and chitin. These may be used alone or in combination of two or more thereof. For example, the bioabsorbable material may be a combination of a synthetic absorbable polymer and a natural absorbable polymer. In particular, the bioabsorbable material is preferably polyglycolic acid, polylactic acid, or a copolymer of lactic acid and caprolactone because these exhibit high strength.

When the bioabsorbable material used is polyglycolide (homopolymer or copolymer of glycolide), the lower limit of the weight average molecular weight of the polyglycolide is preferably 30,000 and the upper limit thereof is preferably 1,000,000. The polyglycolide having a weight average molecular weight of 30,000 or more can more securely reinforce tissue. The polyglycolide having a weight average molecular weight of 1,000,000 or less can further reduce foreign body reaction. The lower limit of the weight average molecular weight of the polyglycolide is more preferably 50,000 and the upper limit thereof is more preferably 300,000.

The fabric layer may be in any form. For example, the fabric layer may be in the form of a knitted fabric, a woven fabric, a nonwoven fabric, or a film. In particular, the fabric layer is preferably a nonwoven fabric from the standpoint of flexibility, air permeability, and ease of staple penetration.

The nonwoven fabric used as the fabric layer may have any areal weight. The lower limit thereof is preferably 3 g/m$^2$ and the upper limit thereof is preferably 300 g/m$^2$. The nonwoven fabric having an areal weight of 3 g/m$^2$ or more can more securely reinforce tissue. The nonwoven fabric having an areal weight of 300 g/m$^2$ or less can further increase adhesion to tissue. The lower limit of the areal weight of the bioabsorbable nonwoven fabric is more preferably 5 g/m$^2$ and the upper limit thereof is more preferably 100 g/m$^2$.

The nonwoven fabric may be produced by any method, and may be produced by any conventionally known method such as electrospinning deposition, melt blowing, needle punching, spunbonding, flash spinning, hydroentanglement, air-laid methods, thermal bonding, resin bonding, or wet methods.

The reinforcement of the present invention includes a sponge layer containing a water-soluble polymer.

Water-soluble polymers exhibit adhesion when containing moisture. Thus, forming a layer containing a water-soluble polymer on the fabric layer allows the reinforcement to be mounted on a surgical stapler simply by soaking the surgical stapler in saline and attaching the reinforcement to a working surface of the surgical stapler. Forming such a layer can also reduce the shifting of the reinforcement during operation of the surgical stapler. Moreover, forming the water-soluble polymer into a sponge allows it to easily absorb moisture and quickly exhibit adhesion. Moreover, since the reinforcement can be mounted by simply attaching it to a working surface of a surgical stapler, the reinforcement does not need to be tubular as conventional reinforcements, and can be used in surgical staplers of various sizes. Furthermore, since the reinforcement is present only on the working surfaces of the surgical stapler, the reinforcement does not get caught on a port when the surgical stapler is inserted into the port. This enables passing the surgical stapler through ports of smaller diameters. The "sponge" herein means a structure having many voids.

Examples of the water-soluble polymer include natural polymers such as polysaccharide materials and protein materials and synthetic polymers such as polyacrylic acid and polyvinyl alcohol. Staple reinforcements for a surgical stapler require highly biocompatible materials because they are embedded in the body. In particular, the water-soluble polymer is preferably a polysaccharide material or a protein material because these materials are less likely to cause shifting during operation of the surgical stapler and have adhesion to a degree that allows easy separation after stapling. Examples of the polysaccharide material include hydroxypropyl methylcellulose, pullulan, sodium alginate, and carboxymethylcellulose. Examples of the protein material include gelatin, collagen peptide, and water-soluble elastin.

The water-soluble polymer in a 2% concentration aqueous solution preferably has a viscosity of 1 mPa·s or higher and 500 mPa·s or lower. The water-soluble polymer having a viscosity within the range can form an appropriately soft sponge layer that exhibits appropriate adhesion after moisture permeates it. Such a sponge layer makes it easy to attach the reinforcement to a surgical stapler.

The sponge layer is preferably a freeze-dried product.

Freeze-drying enables formation of the sponge layer without a pore-forming agent, thus eliminating the need for removal of a pore-forming agent and allowing formation of a sponge layer having high material purity. The method for freeze-drying is not limited, and may be a conventionally known method.

The sponge layer preferably has a thickness of 0.5 mm or more and 10 mm or less.

The sponge layer having a thickness in the range can further reduce shifting during operation of the surgical stapler, and can be easily adjusted to have an appropriate degree of adhesion that allows easy separation after stapling. The thickness of the sponge layer is preferably 1.5 mm or more, while preferably 5.0 mm or less. The thickness of the sponge layer formed by freeze-drying can be adjusted by adjusting the amount of the water-soluble polymer solution with which the fabric layer is soaked. The thickness of the sponge layer herein refers to the average of thicknesses measured across the entire area of the sponge layer using a dial indicator (e.g., SMD-565J-L, produced by Teclock Co., Ltd.) at intervals of one site/cm$^2$.

The sponge layer may have any density, but preferably has a density of 0.04 g/cm$^3$ or higher and 0.2 g/cm$^3$ or lower.

The sponge layer having a density of the range can further reduce shifting during operation of the surgical stapler, and can be easily adjusted to have an appropriate degree of adhesion that allows easy separation after stapling.

In the reinforcement of the present invention, the fabric layer and the sponge layer are integrally laminated.

Integrally laminating the fabric layer and the sponge layer that exhibits adhesion increases handleability, allowing the reinforcement to be easily mounted on a surgical stapler in the operation room. The "integrally laminated" herein means that the fabric layer and the sponge layer are joined to each other to the extent that the layers are less likely to separate from each other even when force is applied. The fabric layer and the sponge layer may be integrally laminated by, for example, a method in which the fabric is floated on a water-soluble polymer solution serving as the material of the sponge layer, followed by freeze-drying. To increase the interfacial adhesion between the fabric layer and the sponge layer, the fabric is preferably hydrophilized with a plasma treatment device or the like so as to improve the permeability of the fabric to the water-soluble polymer solution.

The reinforcement of the present invention preferably has an adhesion strength of 1.5 N/cm$^2$ or higher when attached to a surgical stapler.

The reinforcement having an adhesion strength in the range when attached to a surgical stapler is even less likely to shift during operation of the surgical stapler. The adhesion strength is more preferably 3.0 N/cm$^2$ or higher. The upper limit of the adhesion strength is not limited, but is preferably 30 N/cm$^2$ or lower for easy separation after stapling. The adhesion strength can be specifically measured by the following method.

The reinforcement is cut into a size of 8 mm wide×40 mm long. Only a length of 10 mm is attached to a working surface (anvil side) of a surgical stapler (e.g., Endopath Stapler ECHELON FLEX 60, produced by Ethicon, Inc.) presoaked with saline, and pressed for three minutes so that the reinforcement is adhered to the working surface. Subsequently, the handle of the surgical stapler is mounted on the lower chuck of a tensile tester (e.g., Autograph Precision Universal Tester AG-X Plus, produced by Shimadzu Corporation), and the end of the reinforcement protruding from the surgical stapler is mounted on the upper chuck of the tensile tester. Thereafter, a tensile test is performed at a pulling speed of 100 mm/min, and the maximum load at which shifting occurs is defined as the adhesion strength.

The reinforcement of the present invention may be produced by any method. For example, the reinforcement may be produced by the above method, or may be produced as follows. The fabric is placed on the bottom, and the water-soluble polymer solution is poured onto the fabric after ensuring that the water-soluble polymer solution does not flow to the bottom surface of the fabric. Then, the sponge layer is formed by freeze-drying, whereby the reinforcement is obtained.

The reinforcement of the present invention is mounted on a surgical stapler by soaking the surgical stapler or the reinforcement in moisture and then attaching the reinforcement to the surgical stapler. The moisture is not necessarily pure water, and may be moisture such as saline or a buffer solution as long as it allows the sponge layer to exhibit adhesion.

The reinforcement of the present invention is used to prevent an air leak, a bodily fluid leak, and tissue damage when tissue is stapled with a surgical stapler. FIG. 1 and FIG. 2 schematically illustrate a surgical stapler mounted with conventional reinforcements and a surgical stapler mounted with reinforcements of the present invention. As illustrated in FIGS. 1(a) and 1(b), even when conventional staple reinforcements 2 for a surgical stapler in a tubular shape are mounted on a surgical stapler 1, the reinforcements 2 may have low adhesion due to the gaps near the seams of the reinforcements 2 or the size difference between the reinforcements 2 and the surgical stapler 1, and thus may shift during operation of the surgical stapler. As illustrated in FIG. 1(b), the conventional staple reinforcements 2 for a surgical stapler are tubular, and thus present on portions other than the working surfaces of the surgical stapler 1. As a result, the staple reinforcements 2 for a surgical stapler may get caught on a port when the surgical stapler 1 is passed through the port, or the surgical stapler 1 may not be passed through a port unless the port has a large diameter.

On the other hand, as illustrated in FIGS. 2(a) and 2(b), staple reinforcements 3 for a surgical stapler of the present invention have a structure in which a fabric layer 31 containing a bioabsorbable material and a sponge layer 32 that exhibit adhesion when containing moisture are integrally laminated. The staple reinforcements 3 for a surgical stapler of the present invention can be mounted on the surgical stapler 1 by attaching them such that the sponge layers 32 contact the working surfaces of the surgical stapler 1. The staple reinforcements are thus less likely to shift during operation of the surgical stapler. As illustrated in FIGS. 2(a) and 2(b), the staple reinforcements 3 for a surgical stapler of the present invention can be mounted without being tubular, and thus are less likely to shift regardless of the size of the surgical stapler. As illustrated in FIG. 2(b), the staple reinforcements 3 for a surgical stapler of the present invention are present only on the working surfaces of the surgical stapler. As a result, the reinforcements do not get caught on a port when the surgical stapler is passed through the port, allowing the surgical stapler to be passed through a thinner port than in the case of the conventional staple reinforcements for a surgical stapler. In addition, the reinforcement of the present invention does not exhibit adhesion unless it contains moisture. The reinforcement thus has high handleability during storage and transportation.

Although FIG. 2 illustrates the use of the reinforcement of the present invention in a linear-type surgical stapler, the reinforcement of the present invention may be used not only in linear-type surgical staplers, but also in circular-type surgical staplers.

Advantageous Effects of Invention

The present invention can provide a staple reinforcement for a surgical stapler that can be used in surgical staplers of various sizes, is easily passed through ports, and is less likely to shift during operation of the surgical stapler.

DESCRIPTION OF EMBODIMENTS

Figure 1A:
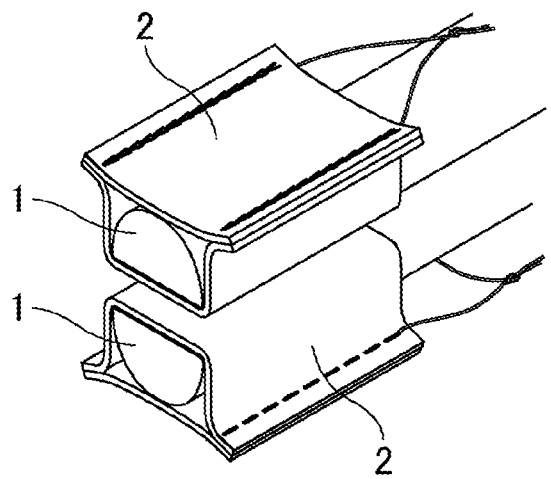
FIG. 1 schematically illustrates exemplary conventional staple reinforcements for a surgical stapler.
Figure 1B:
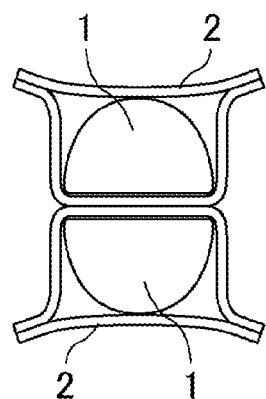
Figure 2A:
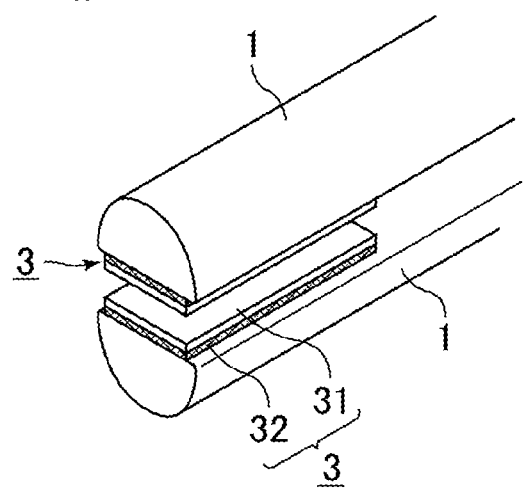
FIG. 2 schematically illustrates exemplary staple reinforcements for a surgical stapler of the present invention.
Figure 2B:
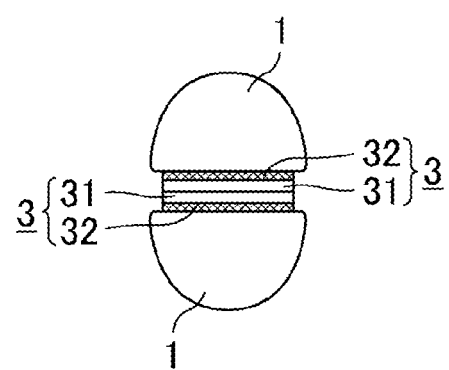

Embodiments of the present invention are described in more detail below. The present invention, however, should not be limited to these embodiments.

Example 1

(1) Production of staple reinforcement for surgical stapler

Distilled water was added to hydroxypropyl methylcellulose (HPMC) (viscosity grade 6: AN6, 2% solution viscosity: 5.1 mPa·s, produced by Mitsubishi-Chemical Foods Corporation) to prepare an 8% by weight HPMC aqueous solution. Then, 10 g of the HPMC aqueous solution was added to a Φ 100 mm petri dish. Next, a sheet-form polyglycolic acid (PGA) nonwoven fabric cut into Φ 100 mm as a fabric layer was floated on the HPMC aqueous solution in the petri dish. After confirming that the HPMC aqueous solution permeated the sheet-form nonwoven fabric, the petri dish was put in a freezer at −80° C. for 15 minutes, whereby the HPMC aqueous solution was frozen. Thereafter, the frozen HPMC aqueous solution was dried by a vacuum freeze dryer to form a HPMC sponge layer (adhesive layer) on the nonwoven fabric, whereby a staple reinforcement for a surgical stapler was prepared. For the obtained staple reinforcement for a surgical stapler, the thickness of the sponge layer was measured by averaging thicknesses measured using a dial indicator (SMD-565J-L, produced by Teclock Co., Ltd.) at intervals of one site/cm². The thickness and weight of the sponge layer were also measured, and the density was calculated. Table 1 shows the results.

(2) Measurement of Adhesion Strength

The reinforcement was cut into a size of 8 mm wide×40 mm long. Only a length of 10 mm was attached to a working surface (anvil side) of a surgical stapler (Endopath Stapler ECHELON FLEX 60, produced by Ethicon, Inc.) presoaked with saline, and pressed for three minutes so that the reinforcement was adhered to the working surface. Subsequently, the handle of the surgical stapler was mounted on the lower chuck of a tensile tester (Autograph Precision Universal Tester AG-X Plus, produced by Shimadzu Corporation), and the end of the reinforcement protruding from the surgical stapler was mounted on the upper chuck of the tensile tester. Thereafter, a tensile test was performed at a pulling speed of 100 mm/min, and the maximum load at which shifting occurred was defined as the adhesion strength. Table 1 shows the results.

Examples 2 to 5

A staple reinforcement for a surgical stapler was obtained as in Example 1 except that the amount of HPMC aqueous solution added to the petri dish was as shown in Table 1. The thickness and density of the sponge layer and the adhesion strength were measured.

Comparative Example 1

Distilled water was added to hydroxypropyl methylcellulose (HPMC) (viscosity grade 6: AN6, 2% solution viscosity: 5.1 mPa·s, produced by Mitsubishi-Chemical Foods Corporation) to prepare an 8% by weight HPMC aqueous solution. Then, 15 g of the HPMC aqueous solution was added to a Φ 100 mm petri dish. Next, a sheet-form polyglycolic acid (PGA) nonwoven fabric cut into Φ 100 mm as a fabric layer was floated on the HPMC aqueous solution in the petri dish. After confirming that the HPMC aqueous solution permeated the sheet-form nonwoven fabric, the petri dish was put in a dryer at 90° C. for 60 minutes to form a HPMC film layer (adhesive layer) on the nonwoven fabric, whereby a staple reinforcement for a surgical stapler was prepared. For the obtained staple reinforcement for a surgical stapler, the thickness and weight of the film layer was measured, and the density was calculated. Table 1 shows the results.

Example 6

Distilled water was added to hydroxypropyl methylcellulose (HPMC) (viscosity grade 50: AN50, 2% solution viscosity: 37 mPa·s, produced by Mitsubishi-Chemical Foods Corporation) to prepare a 6% by weight HPMC aqueous solution. Then, 10 g of the HPMC aqueous solution was added to a Φ 100 mm petri dish. Next, a sheet-form polyglycolic acid (PGA) nonwoven fabric cut into Φ 100 mm as a fabric layer was floated on the HPMC aqueous solution in the petri dish. After confirming that the HPMC aqueous solution permeated the sheet-form nonwoven fabric, the petri dish was put in a freezer at −80° C. for 15 minutes, whereby the HPMC aqueous solution was frozen. Thereafter, the frozen HPMC aqueous solution was dried in a vacuum freeze dryer to form a HPMC sponge layer (adhesive layer) on the nonwoven fabric, whereby a staple reinforcement for a surgical stapler was prepared. For the obtained staple reinforcement for a surgical stapler, the thickness of the sponge layer was measured as in Example 1. The thickness and weight of the sponge layer were also measured, and the density was calculated. Table 1 shows the results.

Examples 7 to 10

A staple reinforcement for a surgical stapler was obtained as in Example 6 except that the amount of HPMC aqueous solution added to the petri dish was as shown in Table 1. The thickness and density of the sponge layer and the adhesion strength were measured.

Comparative Example 2

Distilled water was added to hydroxypropyl methylcellulose (HPMC) (viscosity grade 50: AN50, 2% solution viscosity: 37 mPa·s, produced by Mitsubishi-Chemical Foods Corporation) to prepare a 5% by weight HPMC aqueous solution. Then, 15 g of the HPMC aqueous solution was added to a Φ 100 mm petri dish. Thereafter, a sheet-form polyglycolic acid (PGA) nonwoven fabric cut into Φ 100 mm as a fabric layer was floated on the HPMC aqueous solution in the petri dish. After confirming that the HPMC aqueous solution permeated the sheet-form nonwoven fabric, the petri dish was put in a dryer at 90° C. for 60 minutes to form a HPMC film layer (adhesive layer) on the nonwoven fabric, whereby a staple reinforcement for a surgical stapler was prepared. For the obtained staple reinforcement for a surgical stapler, the thickness and weight of the film layer was measured, and the density was calculated. Table 1 shows the results.

Example 11

Distilled water was added to pullulan (Japanese Pharmacopoeia pullulan, 2% solution viscosity: 3.7 mPa·s, produced by Hayashibara Co., Ltd.) to prepare a 10% by weight pullulan aqueous solution. Then, 20 g of the pullulan aqueous solution was added to a Φ 100 mm petri dish. Next, a sheet-form PGA nonwoven fabric cut into Φ 100 mm as a fabric layer was floated on the pullulan aqueous solution in the petri dish. After confirming that the pullulan aqueous solution permeated the sheet-form nonwoven fabric, the petri dish was put in a freezer at −80° C. for 15 minutes, whereby pullulan aqueous solution was frozen. Thereafter, the frozen pullulan aqueous solution was dried in a vacuum freeze dryer to form a pullulan sponge layer (adhesive layer) on the nonwoven fabric, whereby a staple reinforcement for a surgical stapler was prepared. For the obtained staple reinforcement for a surgical stapler, the thickness and density of the sponge layer and the adhesion strength were measured as in Example 1. Table 1 shows the results.

Examples 12 and 13

A staple reinforcement for a surgical stapler was obtained as in Example 11 except that the amount of pullulan aqueous solution added to the petri dish was as shown in Table 1. The thickness and density of the sponge layer and the adhesion strength were measured.

Example 14

Distilled water was added to sodium alginate (low viscosity grade: IL-2, 2% solution viscosity: 63 mPa·s, produced by Kimica Corporation) to prepare a 10% by weight sodium alginate aqueous solution. Then, 20 g of the sodium alginate aqueous solution was added to a Φ 100 mm petri dish. Next, a sheet-form PGA nonwoven fabric cut into Φ 100 mm as a fabric layer was floated on the sodium alginate aqueous solution in the petri dish. After confirming that the sodium alginate aqueous solution permeated the sheet-form nonwoven fabric, the petri dish was put in a freezer at −80° C. for 15 minutes, whereby sodium alginate aqueous solution was frozen. Thereafter, the frozen sodium alginate aqueous solution was dried in a vacuum freeze dryer to form a sodium alginate sponge layer (adhesive layer) on the nonwoven fabric, whereby a staple reinforcement for a surgical stapler was prepared. For the obtained staple reinforcement for a surgical stapler, the thickness and density of the sponge layer and the adhesion strength were measured as in Example 1. Table 1 shows the results.

Example 15

A staple reinforcement for a surgical stapler was obtained as in Example 14 except that the amount of sodium alginate aqueous solution added to the petri dish was as shown in Table 1. The thickness and density of the sponge layer and the adhesion strength were measured.

Example 16

Distilled water was added to gelatin (MediGelatin HMG-BP, 2% solution viscosity: 2.0 mPa·s, produced by Nippi, Inc.) to prepare a 5% by weight gelatin aqueous solution. Then, 15 g of the gelatin aqueous solution was added to a Φ100 mm petri dish. Next, a sheet-form PGA nonwoven fabric cut into Φ100 mm as a fabric layer was floated on the gelatin aqueous solution in the petri dish. After confirming that the gelatin aqueous solution permeated the sheet-form nonwoven fabric, the petri dish was put in a freezer at −80° C. for 15 minutes, whereby gelatin aqueous solution was frozen. Thereafter, the frozen gelatin aqueous solution was dried in a vacuum freeze dryer to form a gelatin sponge layer (adhesive layer) on the nonwoven fabric, whereby a staple reinforcement for a surgical stapler was prepared. For the obtained staple reinforcement for a surgical stapler, the thickness and density of the sponge layer and the adhesion strength were measured as in Example 1. Table 1 shows the results.

Examples 17 to 19

A staple reinforcement for a surgical stapler was obtained as in Example 16 except that the amount of gelatin aqueous solution added to the petri dish was as shown in Table 1. The thickness and density of the sponge layer and the adhesion strength were measured.
<Evaluation>
The staple reinforcements for a surgical stapler obtained in the examples and the comparative examples were evaluated for the following items. Table 1 shows the results.
(Evaluation of Attachability)
The obtained staple reinforcement for a surgical stapler was cut into a piece of 10 mm wide×60 mm long and a piece of 8 mm wide×60 mm long and attached to the working surfaces (cartridge side and anvil side) of a surgical stapler (Endopath Stapler ECHELON FLEX 60 produced by Ethicon, Inc., diameter: 12 mm) presoaked with saline, such that the sponge layers contacted the surgical stapler. The attachability was evaluated as "Good" when the reinforcement at this time was easily adhered to the working surfaces of the stapler, and "Poor" when the reinforcement was not easily adhered to the working surfaces.
(Evaluation of Ease of Passing Through Port)
The obtained staple reinforcement for a surgical stapler was cut into a piece of 10 mm wide×60 mm long and a piece of 8 mm wide×60 mm long and attached to the working surfaces (cartridge side and anvil side) of a surgical stapler (Endopath Stapler ECHELON FLEX 60 produced by Ethicon, Inc., diameter: 12 mm) presoaked with saline, such that the sponge layers contacted the surgical stapler. The surgical stapler with the staple reinforcement for a surgical stapler attached thereto was then passed through a ϕ 12 mm port. The ease of passing through a port was evaluated as "Good" when the reinforcement at this time did not get caught on the port or separated from the device, and "Poor" when the reinforcement got caught on the port or separated from the device. The evaluation was not performed in Comparative Examples 1 and 2 because the reinforcements could not be mounted on the device.
(Evaluation of Shift Resistance)
The obtained staple reinforcement for a surgical stapler was cut into a piece of 10 mm wide×60 mm long and a piece of 8 mm wide×60 mm long and attached to the working surfaces (cartridge side and anvil side) of a surgical stapler (Endopath Stapler ECHELON FLEX 60 produced by Ethicon, Inc.) presoaked with saline, such that the sponge layers contacted the surgical stapler. Thereafter, a porcine lung was held with the surgical stapler with the staple reinforcement for a surgical stapler attached thereto, and pulled from right to left and up and down. The shift resistance was evaluated as "Good" when the reinforcement at this time did not shift, "Fair" when the reinforcement slightly shifted but the shifting was within a range that does not cause trouble in actual use, and "Poor" when the reinforcement greatly shifted. The evaluation was not performed in Comparative Examples 1 and 2 because the reinforcements could not be mounted on the device.
(Evaluation of Fire Cutting Properties)
A porcine lung was held with the surgical stapler with the staple reinforcement for a surgical stapler attached thereto. The closing lever was squeezed until it locked in place, followed by three strokes of the firing trigger to perform stapling and cutting with the knife. After the knife was returned to the original position in the fourth stroke, the lock of the stapler was released. The fire cutting properties were evaluated as "Good" when the stapling and cutting with the knife were performed without any trouble and the reinforcement was separated from the stapler without any trouble, and "Poor" when the stapling and cutting with the knife failed or the reinforcement was not separated from the stapler. The evaluation was not performed in Comparative Examples 1 and 2 because the reinforcements could not be mounted on the device.

TABLE 1

| | Staple reinforcement for surgical stapler | | | | | | | | | | | |
|---|---|---|---|---|---|---|---|---|---|---|---|---|
| | | Adhesive layer | | | | | | | Evaluation | | | |
| | Fabric layer Material | Material | Viscosity* (mPaS) *in 2% solution | Form | Concentration (%) | Amount of solution (g) | Density (g/cm$^3$) | Thickness (mm) | Adhesion strength (N/cm$^2$) | Attachability | Ease of passing through port | Shift resistance | Fire cutting properties |
| Example 1 | PGA sheet | HPMC | 5.1 | Sponge | 8 | 10 | 0.115 | 0.9 | 1.5 | Good | Good | Fair | Good |
| Example 2 | | | | | | 15 | 0.105 | 1.6 | 4.0 | Good | Good | Good | Good |
| Example 3 | | | | | | 20 | 0.092 | 2.4 | 5.8 | Good | Good | Good | Good |

TABLE 1-continued

Staple reinforcement for surgical stapler

| | Fabric layer Material | Adhesive layer | | | | | | Evaluation | | | | |
| --- | --- | --- | --- | --- | --- | --- | --- | --- | --- | --- | --- | --- |
| | | Material | Viscosity* (mPaS) *in 2% solution | Form | Concentration (%) | Amount of solution (g) | Density (g/cm³) | Thickness (mm) | Adhesion strength (N/cm²) | Attachability | Ease of passing through port | Shift resistance | Fire cutting properties |
| Example 4 | | | | | | 30 | 0.092 | 3.6 | 5.1 | Good | Good | Good | Good |
| Example 5 | | | | | | 40 | 0.088 | 4.9 | 8.3 | Good | Good | Good | Good |
| Comparative Example 1 | | | | Film | | 15 | 1.502 | 0.08 | — | Poor | — | — | — |
| Example 6 | PGA sheet | HPMC | 37 | Sponge | 6 | 10 | 0.068 | 1.0 | 1.8 | Good | Good | Fair | Good |
| Example 7 | | | | | | 15 | 0.071 | 1.7 | 4.6 | Good | Good | Good | Good |
| Example 8 | | | | | | 20 | 0.063 | 2.5 | 5.3 | Good | Good | Good | Good |
| Example 9 | | | | | | 30 | 0.058 | 4.0 | 7.2 | Good | Good | Good | Good |
| Example 10 | | | | | | 40 | 0.062 | 4.9 | 9.7 | Good | Good | Good | Good |
| Comparative Example 2 | | | | Film | | 15 | 2.571 | 0.03 | — | Poor | — | — | — |
| Example 11 | PGA sheet | Pullulan | 3.7 | Sponge | 10 | 20 | 0.136 | 2.4 | 8.6 | Good | Good | Good | Good |
| Example 12 | | | | | | 30 | 0.127 | 3.5 | 12.9 | Good | Good | Good | Good |
| Example 13 | | | | | | 40 | 0.123 | 5.1 | 10.6 | Good | Good | Good | Good |
| Example 14 | PGA sheet | Sodium alginate | 63 | Sponge | 10 | 20 | 0.073 | 2.2 | 3.8 | Good | Good | Good | Good |
| Example 15 | | | | | | 30 | 0.064 | 3.9 | 4.8 | Good | Good | Good | Good |
| Example 16 | PGA sheet | Gelatin | 2.0 | Sponge | 5 | 15 | 0.069 | 1.7 | 5.8 | Good | Good | Good | Good |
| Example 17 | | | | | | 20 | 0.072 | 2.1 | 5.8 | Good | Good | Good | Good |
| Example 18 | | | | | | 30 | 0.070 | 3.7 | 7.1 | Good | Good | Good | Good |
| Example 19 | | | | | | 40 | 0.070 | 4.3 | 6.3 | Good | Good | Good | Good |

INDUSTRIAL APPLICABILITY

The present invention can provide a staple reinforcement for a surgical stapler that can be used in surgical staplers of various sizes, is easily passed through ports, and is less likely to shift during operation of the surgical stapler.

REFERENCE SIGNS LIST 1 surgical stapler
2 conventional staple reinforcement for a surgical stapler
3 staple reinforcement for a surgical stapler of the present invention
31 fabric layer
32 sponge layer

The invention claimed is:

1. A staple reinforcement for a surgical stapler, comprising:
a fabric layer containing a bioabsorbable material; and
a sponge layer consisting of at least one water-soluble polymer selected from the group consisting of hydroxypropyl methylcellulose and sodium alginate,
the fabric layer and the sponge layer being integrally laminated,
the sponge layer being on a side that is configured to adhere to a surface of the surgical stapler where the staple reinforcement is attached to the surgical stapler, and
the sponge layer being a freeze-dried product.

2. The staple reinforcement for a surgical stapler according to claim 1, wherein the bioabsorbable material is polyglycolic acid, polylactic acid, or a copolymer of lactic acid and caprolactone.

3. The staple reinforcement for a surgical stapler according to claim 1, wherein the sponge layer has a thickness of 0.5 mm or more and 10 mm or less.

4. The staple reinforcement for a surgical stapler according to claim 1, which has an adhesion strength of 1.5 N/cm² or higher when attached to the surgical stapler.

5. The staple reinforcement for a surgical stapler according to claim 1, wherein the sponge layer is an adhesive layer that is configured to adhere directly to a surface of the surgical stapler when the staple reinforcement is attached to the surgical stapler.

6. The staple reinforcement for a surgical stapler according to claim 1, wherein the water-soluble polymer in a 2% concentration aqueous solution has a viscosity of 1 mPa·s or higher and 500 mPa·s or lower.

* * * * *